(12) United States Patent
Haffner et al.

(10) Patent No.: US 8,097,859 B2
(45) Date of Patent: Jan. 17, 2012

(54) OXYGEN CONCENTRATION MEASURING DEVICE

(75) Inventors: Ken Yves Haffner, Baden (CH); Julio Danin Lobo, Baden (CH); Juergen Kappler, Frankfurt Main (DE); Thomas Bauer, Bad Homburg (DE)

(73) Assignee: ABB Research Ltd, Zurich (CH)

( * ) Notice: Subject to any disclaimer, the term of this patent is extended or adjusted under 35 U.S.C. 154(b) by 0 days.

(21) Appl. No.: 13/166,628

(22) Filed: Jun. 22, 2011

(65) Prior Publication Data

US 2011/0248178 A1    Oct. 13, 2011

Related U.S. Application Data

(63) Continuation of application No. PCT/EP2008/068259, filed on Dec. 23, 2008.

(51) Int. Cl.
*G01J 1/10* (2006.01)
(52) U.S. Cl. ....................................................... 250/373
(58) Field of Classification Search ............... 250/252.1, 250/362, 372, 373
See application file for complete search history.

(56) References Cited

U.S. PATENT DOCUMENTS

| | | | |
|---|---|---|---|
| 3,738,755 A | 6/1973 | Channey et al. |
| 4,035,083 A | 7/1977 | Woodriff et al. |
| 4,504,145 A | 3/1985 | Koizumi |
| 4,591,721 A | 5/1986 | Wong |

FOREIGN PATENT DOCUMENTS

| | | |
|---|---|---|
| GB | 918878 A | 2/1963 |
| WO | WO 86/02445 A1 | 4/1986 |

OTHER PUBLICATIONS

International Search Report (PCT/ISA/210) issued on Sep. 15, 2009, by European Patent Office as the International Searching Authority for International Application No. PCT/EP2008/068259.
Written Opinion (PCT/ISA/237) issued on Sep. 15, 2009, by European Patent Office as the International Searching Authority for International Application No. PCT/EP2008/068259.

*Primary Examiner* — Mark R Gaworecki
(74) *Attorney, Agent, or Firm* — Buchanan Ingersoll & Rooney PC (57) ABSTRACT

An oxygen concentration measuring device is provided for determining an oxygen concentration of a gas in a sample volume. The device includes an optical device configured for irradiating the sample volume containing oxygen with a first UV radiation intensity, at least one wavelength of which is close to a spectral absorption line of oxygen, a magnetic field generator configured for applying a magnetic field at the sample volume, and a UV light detector configured for measuring a second UV radiation intensity coming from the sample volume. The oxygen concentration in the sample volume is determined on the basis of the applied magnetic field and the measured second UV radiation intensity.

38 Claims, 6 Drawing Sheets

OXYGEN CONCENTRATION MEASURING DEVICE

RELATED APPLICATION

This application claims priority as a continuation application under 35 U.S.C. §120 to PCT/EP2008/068259 filed as an International Application on Dec. 23, 2008 designating the U.S., the entire content of which is hereby incorporated by reference in its entirety

FIELD

The present disclosure relates to an oxygen measuring device. More particularly, the present disclosure relates to a measuring device which detects an oxygen concentration within a gas sample volume.

BACKGROUND INFORMATION

Gas concentration measurement can be provided by means of light absorption, where the absorbed light has an appropriate wavelength or an appropriate range of wavelengths. Oxygen gas is an important gas present, for example, in combustion processes. Residual oxygen detection in combustion processes, for example, yields valuable information for emission monitoring. Furthermore, the measurement of an oxygen concentration in the presence of other gases has abundant applications in the medical field.

In many cases, oxygen concentrations present in an ambient gas may be very low such that a sensitive oxygen concentration measuring device is required.

SUMMARY

An exemplary embodiment of the present disclosure provides an oxygen concentration measuring device configured for determining an oxygen concentration of a gas in a sample volume containing oxygen. The oxygen concentration measuring device includes an optical device configured for irradiating the sample volume with a first UV radiation having a first UV radiation intensity. The optical device includes a UV light source configured for emitting the first UV radiation, where the first UV radiation including at least one wavelength which is close to a spectral absorption line of oxygen. The oxygen concentration measuring device includes a magnetic field generator configured for applying a magnetic field at the sample volume, and a UV light detector configured for measuring a second UV radiation intensity of a second UV radiation coming from the sample volume. The oxygen concentration measuring device also includes an evaluation unit configured for determining the oxygen concentration in the sample volume on the basis of the applied magnetic field and the measured second UV radiation intensity, and a reference cell which contains oxygen of a reference concentration. The evaluation unit is configured for receiving a measured oxygen concentration reference signal indicative of the oxygen concentration in the reference cell, and for determining the oxygen concentration in the sample volume on the basis of the oxygen concentration reference signal.

An exemplary embodiment of the present disclosure provides a method for determining an oxygen concentration in a sample volume containing oxygen. The exemplary method includes emitting a first UV radiation from a UV light source towards the sample volume, where the UV radiation includes at least one wavelength which is close to a spectral absorption line of oxygen. The exemplary method includes irradiating the sample volume with the first UV radiation, applying a magnetic field at the sample volume, and measuring the intensity of a second UV radiation coming from the sample volume. In addition, the exemplary method includes determining the oxygen concentration in the sample volume on the basis of the applied magnetic field and the measured intensity of the second UV radiation. The exemplary method also includes performing a calibration of the evaluated signal versus an actual oxygen concentration at least one of continuously and intermittently during operation by reference measurements with a reference oxygen cell.

An exemplary embodiment of the present disclosure provides a method for determining an oxygen concentration in a sample volume containing oxygen. The exemplary method includes emitting a first UV radiation from a UV light source towards the sample volume, where the UV radiation includes at least one wavelength which is close to a spectral absorption line of oxygen. The exemplary method includes irradiating the sample volume with the first UV radiation, applying a magnetic field at the sample volume, and measuring the intensity of a second UV radiation coming from the sample volume. In addition, the exemplary method includes determining the oxygen concentration in the sample volume on the basis of the applied magnetic field and the measured intensity of the second UV radiation. The exemplary method also includes performing a calibration of the evaluated signal versus an actual oxygen concentration at least one of continuously and intermittently during operation by reference measurements with a reference oxygen cell.

BRIEF DESCRIPTION OF THE DRAWINGS

Additional refinements, advantages and features of the present disclosure are described in more detail below with reference to exemplary embodiments illustrated in the drawings, in which.

DETAILED DESCRIPTION

Exemplary embodiments of the present disclosure provide an oxygen concentration measuring device for determining an oxygen concentration of a gas in a sample volume is provided. The oxygen concentration measuring device includes an optical device configured for irradiating the sample volume containing oxygen with a first UV radiation intensity. The optical device includes a UV light source configured for emitting the first UV radiation intensity, where the UV radiation including at least one wavelength which is close to a spectral absorption line of oxygen. The optical device also includes a magnetic field generator configured for applying a magnetic field at the sample volume, and a UV light detector configured for measuring a second UV radiation intensity coming from the sample volume. In addition, the optical device includes an evaluation unit configured for determining the oxygen concentration in the sample volume on the basis of the applied magnetic field and the measured second UV radiation intensity.

An exemplary embodiment of the present disclosure provides a method for determining an oxygen concentration in a sample volume. The method including the steps of: emitting a first UV radiation from a UV light source towards the sample volume, where the UV radiation includes at least one wavelength which is close to a spectral absorption line of oxygen; irradiating the sample volume containing oxygen with the first UV radiationl applying a magnetic field at the sample volume; measuring the intensity of a second UV radiation coming from the sample volume; and determining the oxygen concentration in the sample volume on the basis of the applied magnetic field and the measured intensity of the second UV radiation.

Reference will now be made in detail to the various exemplary embodiments, one or more examples of which are illustrated in the drawings. Each example is provided by way of explanation and is not meant as a limitation. For example, features illustrated or described as part of one embodiment can be used on or in conjunction with other embodiments to yield yet a further embodiment. It is intended that the present disclosure includes such modifications and variations.

A number of exemplary embodiments will be explained below. In this case, identical structural features are identified by identical reference symbols in the drawings. The structures shown in the drawings are not depicted true to scale but rather serve only for the better understanding of the illustrated exemplary embodiments.

Figure 1:
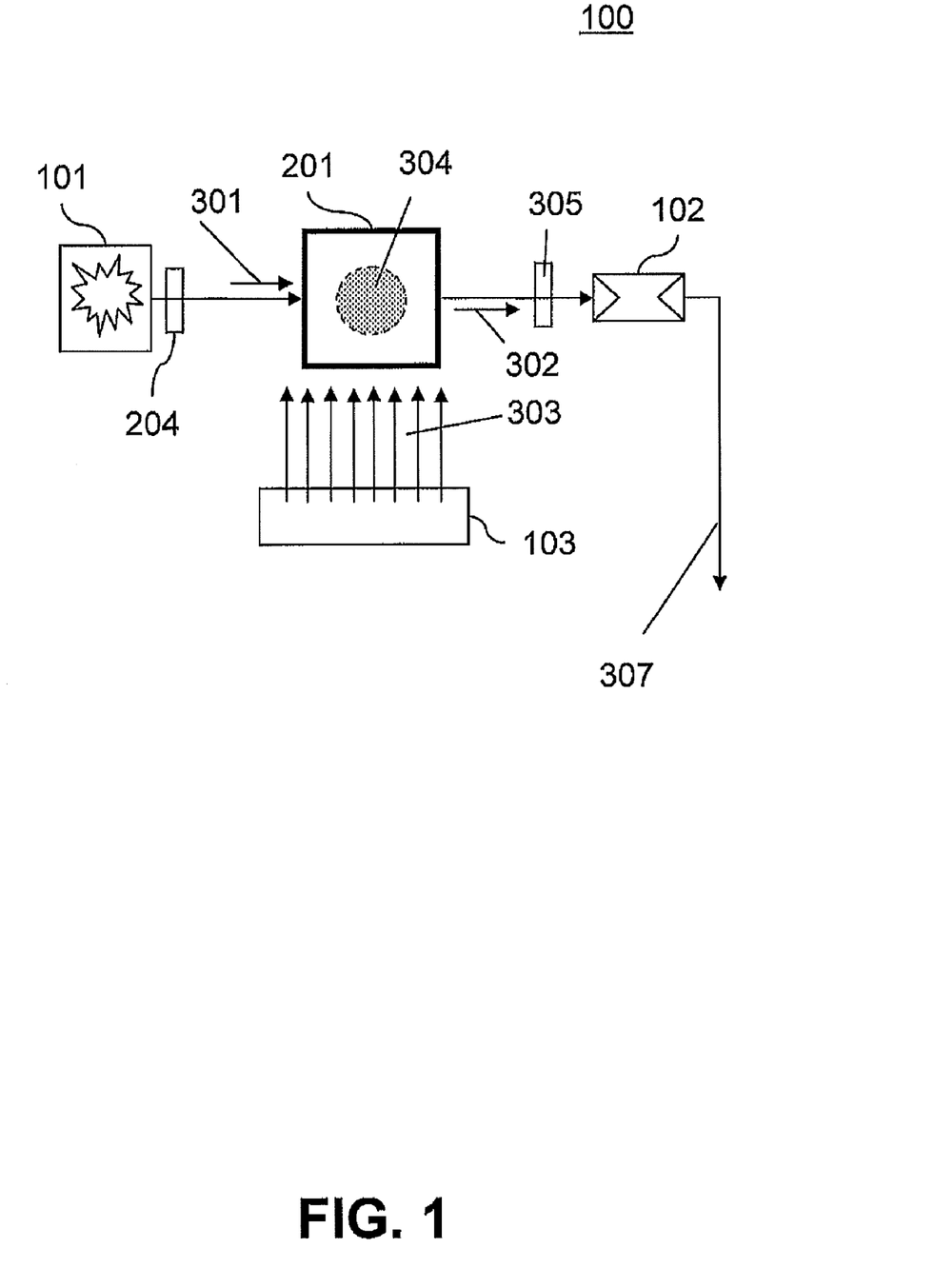
FIG. 1 illustrates a schematic block diagram for explaining the principle of an oxygen concentration measurement based on the application of a magnetic field at a sample volume of oxygen to be measured, according to an exemplary embodiment of the present disclosure.

FIG. 1 is a block diagram illustrating a principle set-up for a measuring device 100 configured for measuring an oxygen concentration within a sample volume 304, according to an exemplary embodiment of the present disclosure. The sample volume 304 can be accessed by an optical UV sensor system and is contained in a sample cell 201 which has UV (ultraviolet) light transmitting windows. Ultraviolet light emitted by an ultraviolet light source 101 is transmitted into the sample cell and is partially absorbed by oxygen contained in the sample volume 304.

It is noted here that outside the sample volume 304 and within the sample cell 201 vacuum, nitrogen gas, or another appropriate medium which does not interfere with the oxygen concentration measurement may be provided. Furthermore, a flow of oxygen through the sample cell 201 may be provided such that a continuous measurement of the oxygen concentration in the flow is possible.

A first UV radiation intensity 301 is chosen such that at least one of its wavelengths essentially corresponds to at least one absorption line of oxygen to be measured. If part of the first UV radiation intensity 301 is absorbed by oxygen contained in the sample volume 304, a second UV radiation intensity 302 is emitted which is lower than the first UV radiation intensity 301 by an amount which has been absorbed in the sample volume 304. The second UV radiation intensity 302 is detected by a UV light detector 102, which converts the detected radiation intensity into a measurement signal 307 which is output from the oxygen concentration measuring device and which is a measure for an oxygen concentration contained in the gas within the sample volume 304.

According to an exemplary embodiment, if the wavelength of the radiation, e.g., the first UV radiation intensity 301, is close to an absorption line of a gas to be measured (in this case oxygen), an absorption cross-section for absorbing the incident radiation can be significant. Especially at short wavelengths in the UV spectral range, UV light absorption by oxygen occurs. An example of oxygen absorption lines is the OI line at 130.2 nm or the absorption line at 184.9 nm. If a wavelength of the first UV radiation intensity 301 is close to this line, an absorption cross-section becomes high.

As used herein, the term "close to" or "essentially corresponds to" a wavelength means that a respective emission line emitted by the UV light source 101 and at least one absorption line of oxygen to be measured are overlapping in their respective wavelengths, at least partially. Such an overlapping of lines having wavelengths being close to each other may occur because an emission line and/or an absorption line do not represent a single wavelength, but exhibit a distribution of wavelengths around a center wavelength (e.g., the wavelength of 130.2 nm or 184.9 nm). Instead of a stationary distribution, the wavelength may also change in time, for example, due to an influence of a magnetic field. The temporal change (fluctuations or controlled change) of the wavelength can also be considered as leading to a wavelength distribution in the above sense.

This distribution of wavelengths of emission and/or absorption lines results from a line broadening which may be due to at least one of natural line broadening, Doppler broadening (temperature movement of atoms and/or molecules), Stark broadening (due to an electric field interacting with respective atoms and/or molecules), etc. Thus, a radiation absorption of oxygen not only occurs at a single wavelength of 130.2 nm or 184.9 nm, but in a spectral region in the range of, e.g., 129 nm to 131 nm or 184 nm to 186 nm, respectively.

Absorption lines of oxygen occur in different spectral regions. Oxygen, e.g., has absorption lines corresponding to the emission lines of a mercury lamp, e.g. near 184 nm and/or 187 nm. Thus, a mercury lamp may be provided as the UV light source 101. Furthermore, a UV laser, which may be tunable and may be adjusted such that its emission wavelength corresponds to an appropriate spectral absorption line of oxygen, is appropriate for the oxygen concentration measurement. In general, the wavelength range in which an absorption may occur is described by the half-width of an absorption line.

An irradiation of the sample volume 304 by a first radiation intensity 301 which includes UV light has the advantage that an absorption cross-section which defines the amount of radiation absorption can be very high in the UV spectral region, e.g., much higher than in the visible spectral region. The following equation (1) gives an estimation of this relation.

$$\rho_{s,UV} \sim 10^4 \cdot \rho_{s,VIS} \tag{1}$$

As indicated by the above equation (1), an operation of the oxygen concentration measuring device in the UV spectral region increases an absorbed radiation intensity as compared to the visible spectral region, and thus, a sensitivity of the detection system is increased by up to four orders of magnitude.

The visible spectral region includes wavelengths between approximately 380 nm and 780 nm, whereas UV radiation includes wavelengths below 380 nm. In this part of the electromagnetic spectrum (below 380 nm), the photon energy is higher than in the visible spectral region. This kind of UV light is partially transmitted via air, whereas glass absorbs radiation in this wavelength spectrum. Optical systems are designed using quartz glass windows which are transparent for visible and UV light. Below a wavelength of 200 nm, ambient air itself absorbs the incident UV radiation, because water vapor is highly absorbent at these short wavelengths. In order to detect a radiation absorption in the UV spectral range in the sample volume 304, the radiation may be transmitted to and detected from the sample volume by using evacuated optical channels.

A magnetic field 303 is applied at the sample volume 304 via a lower part of the sample cell 201 (shown in FIG. 1), or by using a solenoid coil the center of which is the sample cell 201. Under the influence of this magnetic field 303, an oxygen absorption line may split into sets of components of shorter and longer wavelengths as compared to a center wavelength obtained with no magnetic field 303. This line splitting is in accordance with the Zeeman effect, which is known as such to the skilled person.

The magnetic field lines may be parallel to the propagation direction of the first UV radiation intensity 301. According to an exemplary embodiment, the UV absorption line is split into two separate lines by the effect of the applied magnetic field 303. In accordance with the Zeeman effect, one of these lines is right-handed polarized, whereas the other of these two lines is left-handed polarized. In order to distinguish between the intensities of these two polarized lines, a polarization analyzer 305 is provided in the exit path, e.g., in the radiation path between the sample volume 304 and the UV light detector 102. The UV light source 101 may emit polarized radiation or the UV light emitted by the UV light source may be polarized by means of a polarizing element 204.

As the magnetic field 303 is generated by a magnetic field generator 103, the magnetic field 303 may be switched on and off periodically. This results in the advantage that a Zeeman splitting of an absorption line of oxygen may be present (magnetic field 303 switched on) or not present (magnetic field 303 switched off). Thus, the relation between the wavelength of the first UV radiation intensity 301 incident onto the sample volume 304 and the wavelength of the absorption line of oxygen to be measured varies in accordance with the presence of the magnetic field 303. Furthermore, the second UV radiation intensity varies in accordance with the variation of the magnetic field 303, because an absorption of the first UV radiation intensity 301 is dependent on a wavelength difference between the incident wavelength and the absorption wavelength of oxygen.

In accordance with an exemplary embodiment, the oxygen concentration within the sample volume 304 may be determined on the basis of different measurement procedures. The underlying principle of a first kind of measurement procedure is a comparison of at least one measurement wherein an absorption of UV radiation by oxygen occurs, with at least one measurement in which an absorption of this UV radiation is decreased or is not present at all. Then, by evaluating the difference in absorption, e.g., the difference between both measurements, a high-contrast signal for the oxygen concentration can be obtained, because other effects on the signal cancel each other in the difference signal.

According to an exemplary embodiment described below, a wavelength of the first UV radiation which is emitted by the UV light source 101 may be held essentially constant throughout the measurement, whereas the oxygen absorption line is Zeeman-shifted by the magnetic field 303 during at least one measurement. Then, during at least one measurement, the magnetic field may be tuned close to an "absorption" value such that the Zeeman shift causes the oxygen absorption line to essentially coincide or overlap with the wavelength of the first UV radiation. During another measurement, the absence of such a Zeeman shift (absence of the magnetic field 303 or magnetic field 303 tuned away from the "absorption" value) may cause the oxygen absorption line not to coincide or overlap with the wavelength of the first UV radiation. Due to the change in absorption between these measurements, the second UV radiation intensity incident onto the UV light detector varies in accordance the magnetic field variation. Thus, resulting variations in the measurement signal 307 depend on a radiation absorption by oxygen and thus on the oxygen concentration in the sample volume 304.

If known oxygen concentrations in the sample volume 304 can be provided and the corresponding variations in the measurement signal 307 are acquired, the oxygen concentration measuring device 100 can be calibrated. This calibration can be provided as a table or function, which relates measurement signal variations to corresponding oxygen concentrations within the sample volume 304.

According to an exemplary embodiment, the UV light source 101 may be provided as a gas discharge lamp, e.g. a mercury lamp, a deuterium lamp, or a combination thereof, such as a combined deuterium-mercury lamp. Instead of or in addition to applying a magnetic field at the sample volume, a magnetic field may be applied at the gas discharge of the UV light source 101. A Zeeman shift is provided by the magnetic field applied at the UV light source 101, and this Zeeman shift may cause at least one wavelength of the first UV radiation emitted by the gas discharge lamp to essentially coincide with the oxygen absorption line. Furthermore, an absence of the magnetic field, i.e. no Zeeman shift, may cause the wavelength of the first UV radiation not to coincide with the oxygen absorption line, or vice versa. The modified absorption with and without a magnetic field again results in variations of the measurement signal 307, and these variations are a function of the oxygen concentration in the sample volume 304. Again, known oxygen concentrations in the sample volume 304 can be provided and corresponding variations in the measurement signal 307 can be monitored such that a calibration of the entire measuring device may be carried out as described above.

In accordance with an exemplary embodiment, at least one polarization state of the second UV radiation incident onto the UV light detector 102 may be analyzed. In this case, the magnetic field applied at the sample volume 304 or at the UV light source 101 is kept at a constant value which is appropriate for providing a sufficient Zeeman shift. Due to the Zeeman effect, the polarization states of the components upshifted and downshifted in wavelength may be different with respect to each other. For example, the upshifted and downshifted components exhibit circular polarizations of opposite handedness. A wavelength of the first UV radiation, which is emitted by the UV light source 101, may coincide with the upshifted component of the oxygen absorption line, whereas the downshifted component only minimally coincides with the oxygen absorption line, or vice versa. Due to the modified absorption of incident first UV radiation intensity at the upshifted and downshifted components, respectively, the second UV radiation intensity incident onto the UV light detector varies accordingly. Thus, resulting variations in the measurement signal 307 outputted from the UV light detector 102 may be utilized to evaluate the oxygen concentration in the sample volume 304, in a similar manner as described above with respect to the variations of the magnetic field applied at the sample volume 304 and/or at the UV light source 101. According to an exemplary embodiment, a polarizing element 204 may then be used in the propagation path of the second UV radiation coming from the sample volume 304 in order to alternately select the two different polarization states mentioned above, e.g., circular polarizations of opposite handedness (e.g., a left circularly or a right circularly polarization state is selected).

In accordance with an exemplary embodiment, more than two different kinds of measurements can be compared in order to obtain even more signal contrast. For example, the absorption can be measured while the magnetic field is changed continuously between two limiting values, and hence the absorption spectrum can be measured as a continuous function of the magnetic field. In this case, the distribution of absorption values is characterized by statistical quantities (such as mean variance, higher-order variances). This allows a particularly stable signal.

According to an exemplary embodiment, at least one of the different kinds of measurements is performed more than once, and may be performed periodically. This allows for obtaining an even more stable signal, because signal fluctuations are averaged statistically. The periodical measurement can, for example, be performed using a lock-in technique, such as described further below. An evaluation of the measurement signals by means of an evaluation unit (described herein with respect to FIGS. 2-5, for example) may be performed by adjusting the wavelength of the UV light source 101 such that it coincides with an oxygen absorption wavelength in such a way that the Zeeman-effect induced shifts of the oxygen absorption line for left and right circularly polarized radiation cause a difference in absorption for the measured left and right circularly polarized waves. Then, both measurement signals can be evaluated, e.g., by forming their ratio or forming their difference over their sum, and can then be used as a highly sensitive measure of the oxygen concentration. In addition, for this purpose, a calibration of the evaluated signal versus an actual oxygen concentration may be carried out, e.g. a priori for a given measurement setup, or continuously or intermittently during operation by reference measurements with a reference oxygen cell 206, as indicated in FIG. 5 described in more detail below. In addition, the relevant emitted spectral radiation intensity can be monitored and can be used for signal evaluation.

In order to increase a signal-to-noise ratio, a lock-in detection mode may be employed which is described below with reference to the exemplary embodiment of FIG. 2. An oxygen concentration in the sample volume 304 may then be determined on the basis of changes in the second UV radiation intensity 302, if the intensity of the magnetic field 303 is varied, e.g., switched on and off.

Furthermore, it is possible to provide a sinusoidal modulation of the magnetic field. The sinusoidal modulation has the advantage that the design of the magnetic field generator is facilitated and that a frequency for changing the magnetic field 303 may easily be adjusted by means of a frequency generator, for example.

Moreover, the magnetic field may be periodically reversed in polarity. This kind of polarity change has the strongest influence on the Zeeman line splitting such that the polarization analyzer 305 may alternately select the set of the longer or upshifted components or the set of the shorter or downshifted components and pass the selected set to the UV light detector 102.

Thus, by changing the intensity of the magnetic field 303 by means of the magnetic field generator 103, the measurement signal 307 varies in accordance with the variation of the magnetic field 303. This variation is due to the fact that a Zeeman shift of the UV oxygen absorption line causes a variation in the absorption such that the second UV radiation intensity 302 is varied, while the first UV radiation intensity 301 is kept at a constant incident wavelength and intensity.

Figure 2:
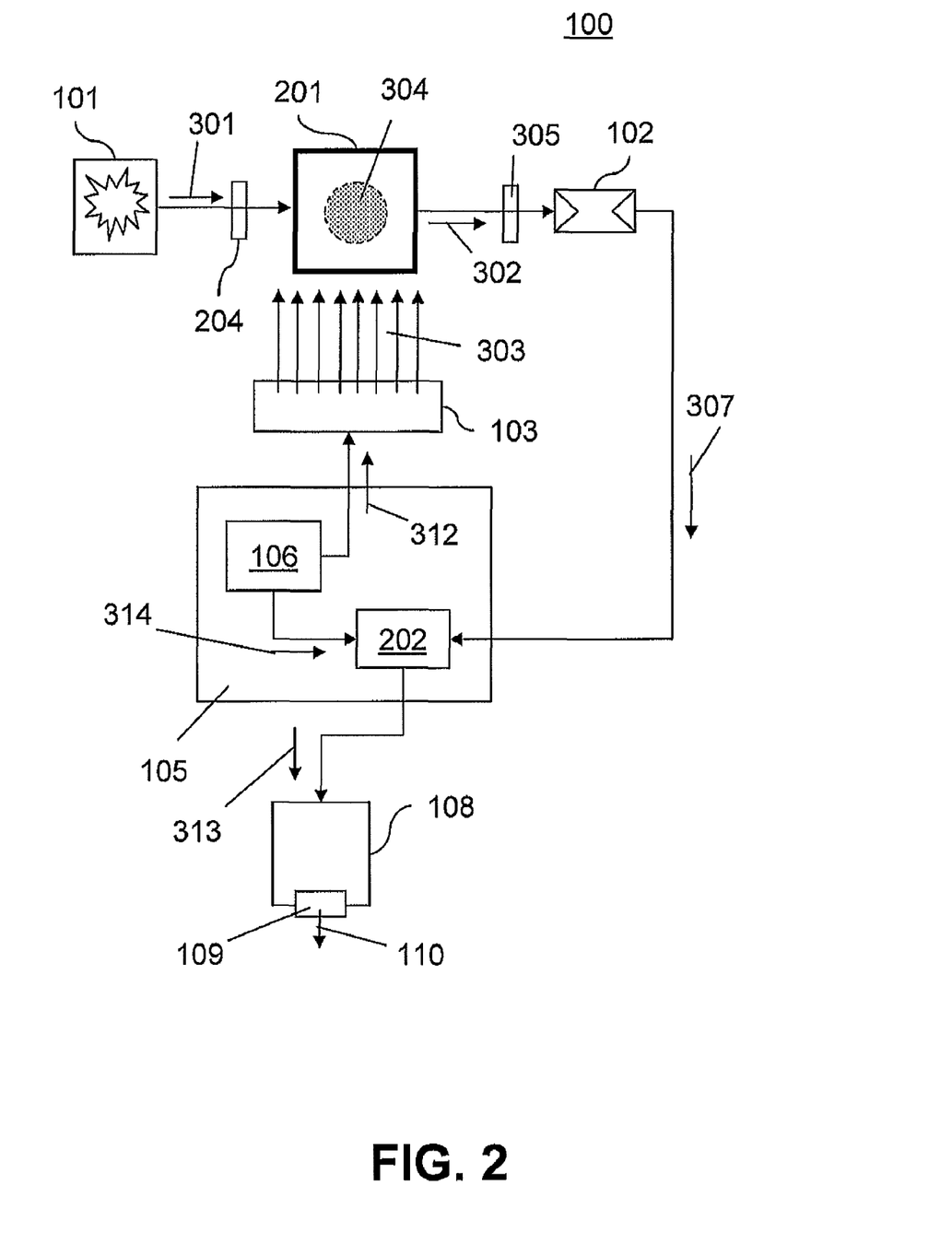
FIG. 2 is a block diagram illustrating a control structure for an oxygen concentration measuring device using a lock-in detection technique, according to an exemplary embodiment of the present disclosure.

FIG. 2 is a block diagram illustrating a lock-in signal detection technique for obtaining the measurement signal 307 described with respect to FIG. 1, according to an exemplary embodiment of the present disclosure. As shown in FIG. 2, a control unit 105 is provided which generates a modulation signal 312 for controlling the magnetic field generator 103. The control unit 105 receives the measurement signal 307 described herein above with respect to FIG. 1. The light source 101 emits the first UV radiation intensity 301 towards the sample volume 304 within the sample cell 201. As explained with respect to FIG. 1, a modulated second UV radiation intensity 302 is obtained if the magnetic field 303 is modulated. Thus, the control unit 105 is configured for correlating the frequency of the modulation signal 312 to the frequency of the measurement signal 307 in order to provide a phase sensitive detection.

The control unit 105 includes a frequency generator unit 106 configured for generating the modulation signal 312 provided for the magnetic field generator 103. It is noted here that the modulation signal 312 may include a sinusoidal modulation, an on/off-switching or any other modulation known to the skilled person. Furthermore, the control unit 105 includes a phase comparator unit 202 configured for comparing phases of two input signals. One input signal of the phase comparator unit 202 is a frequency signal 314 provided by the frequency generator unit 106. The frequency signal 314 corresponds to the modulation signal 312 with respect to its frequency.

According to an exemplary embodiment, the second signal input into the phase comparator unit 202 is the measurement signal 307 output from the UV light detector 102. The phase comparator unit 202 compares the phases of the two input signals and outputs a lock-in signal 313 which is based on a correlation of the two input signals of the phase comparator unit. The control unit 105 thus provides an enhancement of the signal-to-noise ratio for the oxygen concentration measurement using the oxygen concentration measuring device 100, because only components of the measurement signal 307 which have a fixed phase relation with respect to the modulation signal 312 are amplified and output as the lock-in signal.

Other contributions in the measurement signal 307 which are not correlated to the frequency and phase of the modulation signal 312, e.g., noise and other interference, are cancelled out by the phase comparator unit 202. The lock-in signal 313 is input into an evaluation unit 108 which evaluates, on the basis of the lock-in signal 313, an output signal indicating the amount of UV absorption in the sample volume 304. The output signal 110 is output via an output unit 109. The output signal 110 is a direct measure of the oxygen concentration within the sample volume 304, because it reflects an absorption of the first UV radiation intensity 301 correlated to the magnetic field variation (magnetic field modulation) 303 provided by the magnetic field generator 103.

Figure 3:
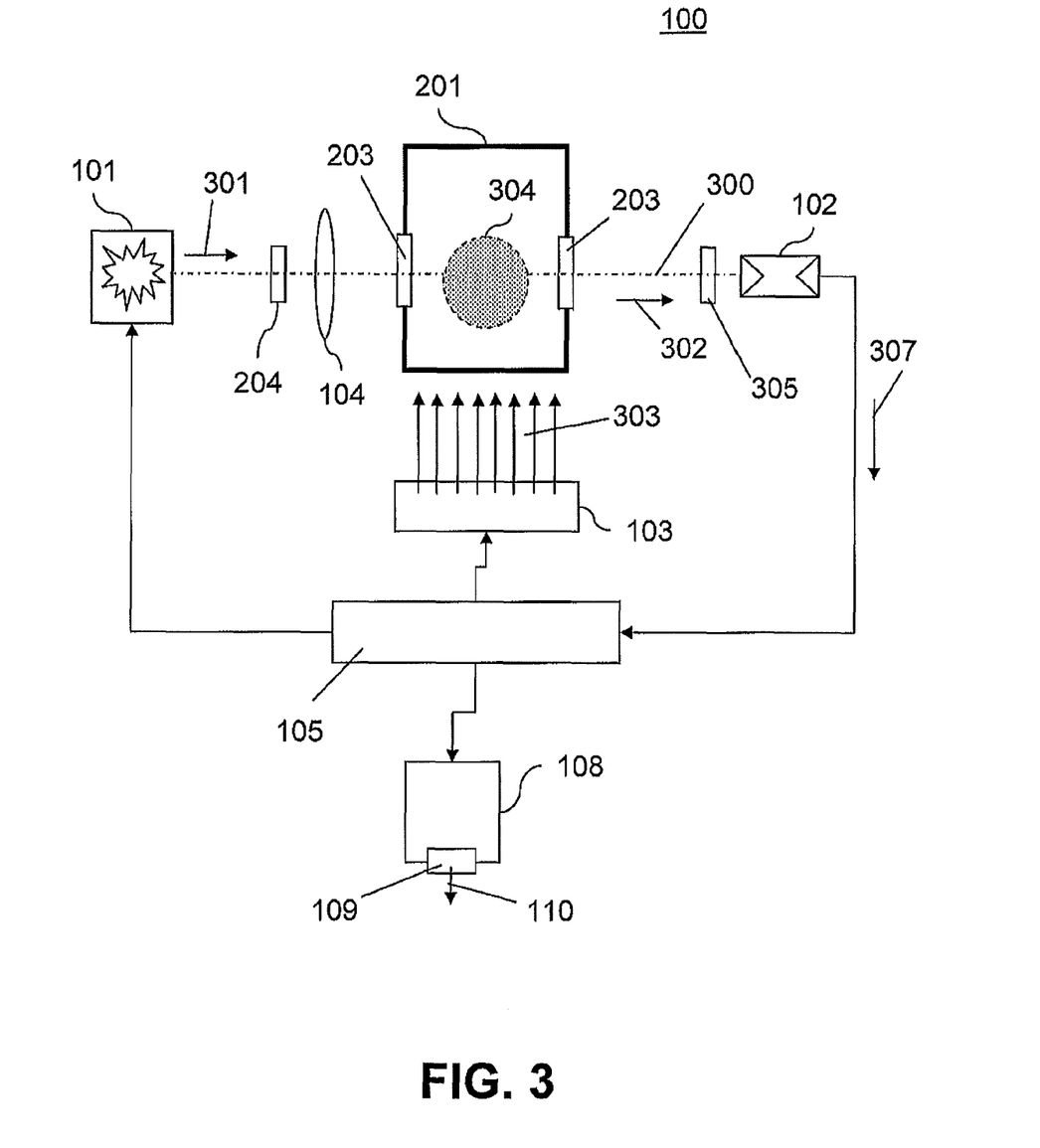
FIG. 3 is a detailed block diagram illustrating an optical set-up of an oxygen concentration measuring device according to an exemplary embodiment of the present disclosure.

FIG. 3 is a more detailed block diagram of an oxygen concentration measuring device 100 according to an exemplary embodiment of the present disclosure. It is noted here that in FIGS. 3, 4 and 5, the dotted lines correspond to optical paths, wherein the solid lines having an arrow correspond to electrical paths. The parallel arrows indicated by reference numeral 303 correspond to a magnetic field 303 which may be oriented parallel to the propagation direction of the first UV radiation intensity 301 and/or the second UV radiation intensity 302.

The first UV radiation intensity 301 emitted from the UV light source 101 is directed onto an optical focusing unit 104 such as a lens configured for directing and focusing the first UV radiation intensity right into the center of the sample volume 304 contained in the sample cell 201. After the first UV radiation intensity 301 has been partially absorbed by the oxygen contained in the sample volume 304, the UV radiation intensity is emitted as a second UV radiation intensity 302 towards the UV light detector 102 via the polarization analyzer 305 (described herein above with respect to FIG. 1).

In accordance with an exemplary embodiment, UV transmissive windows 203 may be provided for transmission of UV radiation intensity through the sample cell 201. Depending on the wavelengths of the first and second UV radiation intensities, materials such as fused silica or quartz glass, for example, may be provided as materials for the UV transmissive windows 203. If the wavelength of the UV radiation intensity is within the range of 200 nm to 100 nm, magnesium difluoride and lithium fluoride may be provided as materials for the UV transmissive windows 203 in order to permit a transmission of the first and second UV radiation intensities.

Figure 4:
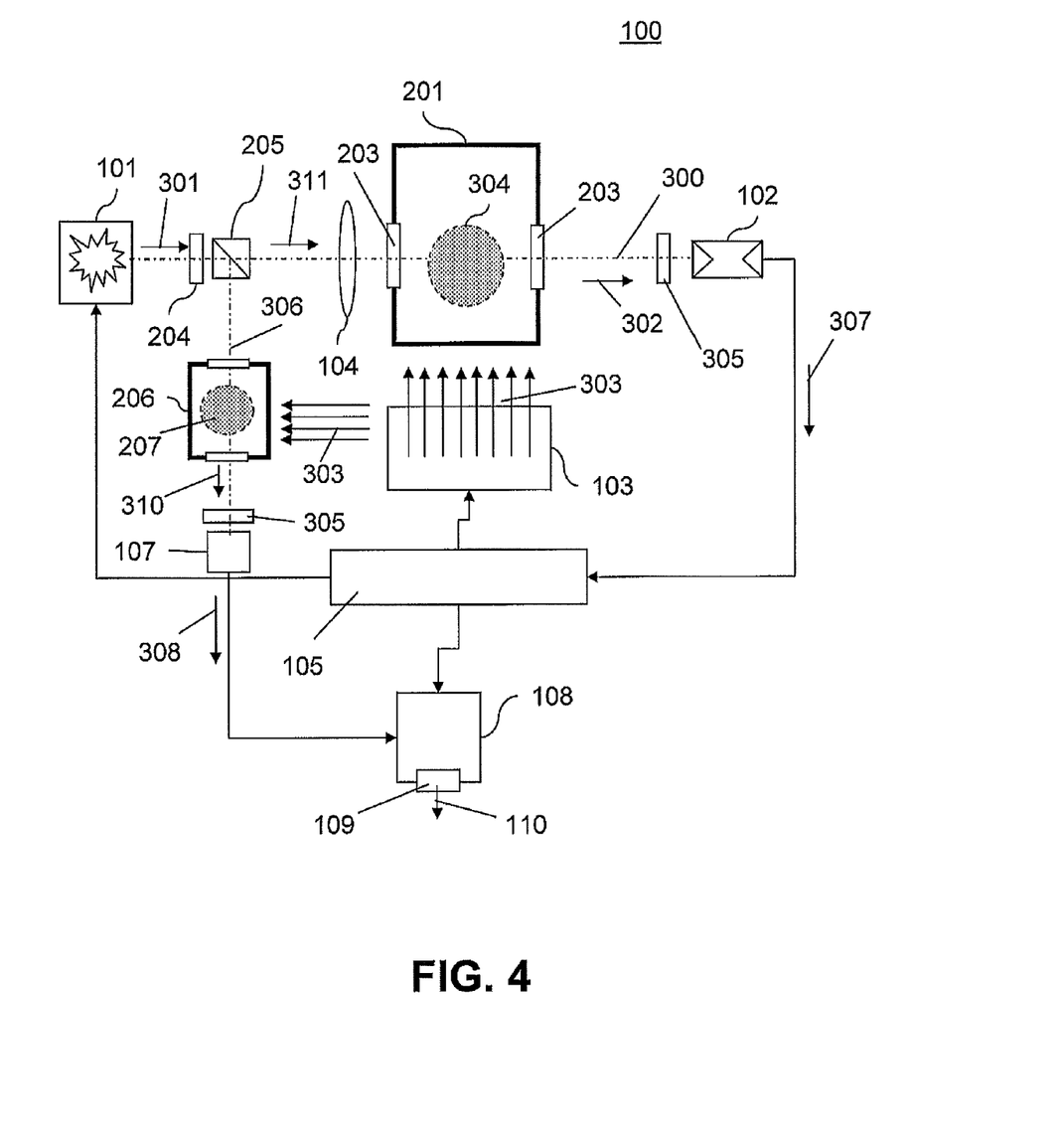
FIG. 4 is a detailed block diagram illustrating a set-up of an oxygen concentration measuring device having a reference light detector according to an exemplary embodiment of the present disclosure.
Figure 5:
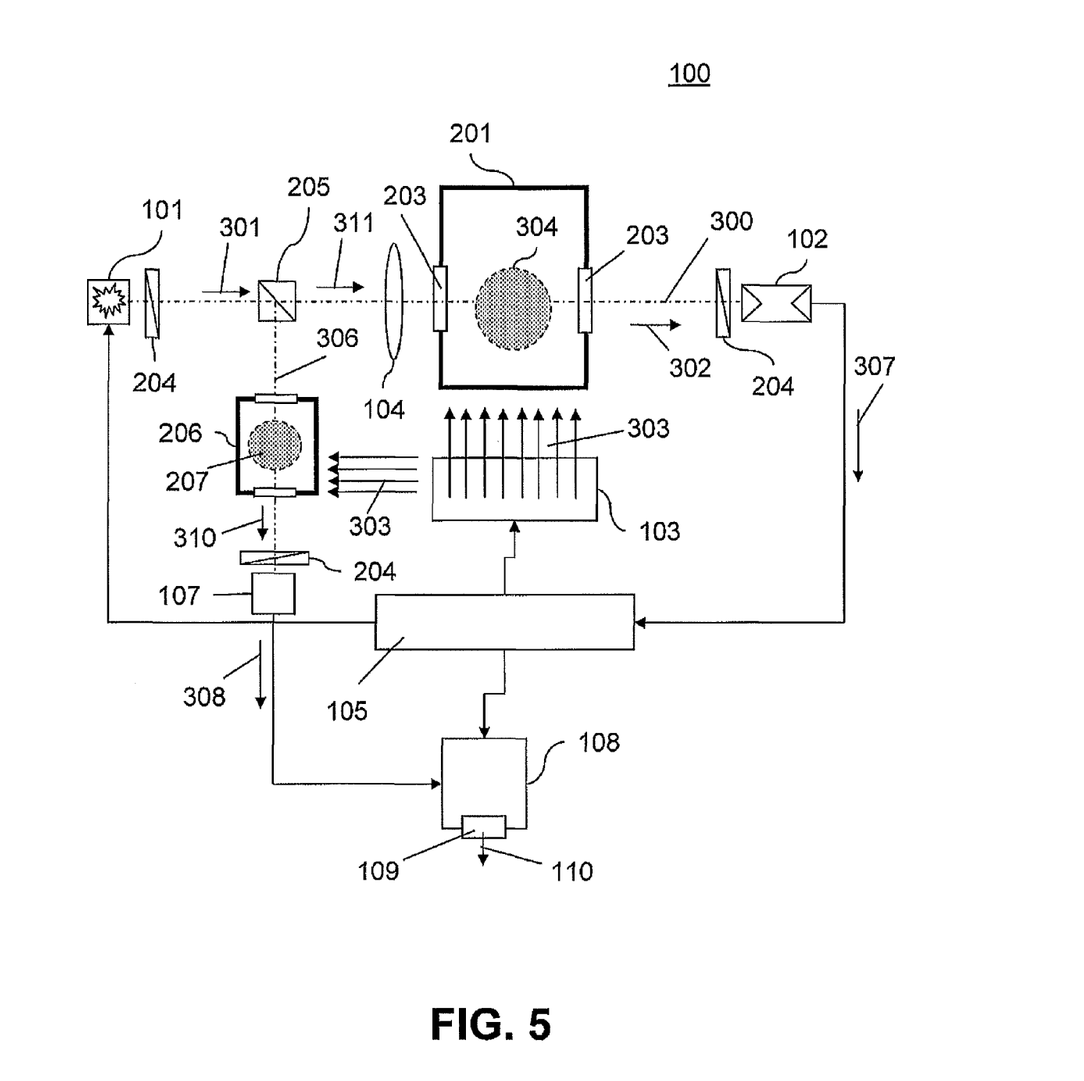
FIG. 5 is a block diagram illustrating the set-up of an oxygen concentration measuring device according to an exemplary embodiment of the present disclosure.

FIG. 4 is a detailed diagram of an oxygen concentration measuring device according to an exemplary embodiment of the present disclosure. It is noted here that parts or components which have been described already with respect to previous drawings are not repeated in the description and in the following drawings in order to avoid a redundant description.

As shown in FIG. 4, the control unit 105 is used to control the magnetic field generator 103 and the UV light source 101. The UV light source 101 may be switched on and off in accordance with required operating conditions. In contrast to the exemplary embodiment shown with respect to FIG. 3 described above, the exemplary embodiment of FIG. 4 includes a reference UV light detector 102 which receives a reference radiation intensity in order to determine an oxygen concentration in the sample volume 304 on the basis of a reference signal 308 which is provided by the reference UV light detector 102.

The generation of the reference signal 308 will now be described in detail. The optical set-up of the oxygen concentration measuring device 100 according to FIG. 4 includes two optical paths, e.g., an optical axis 300 which connects the UV light source 101 via the sample volume 304 to the UV light detector 102.

A second optical axis, e.g., a reference detector optical axis 306, is provided in an orientation perpendicular to the optical axis 300. A portion of the first UV radiation intensity 301 is directed to a reference cell 206 which contains a known oxygen concentration within a reference volume 207. The portion of the first UV radiation intensity 306 is directed along the reference detector optical axis 306 via a polarization analyzer 305 towards the reference UV light detector 107. The reference UV light detector 107 receives a reference radiation intensity 310 in accordance with absorption processes which take place in the reference volume 207 having a known and fixed oxygen concentration. Except that the oxygen concentration in the reference cell 206 is known, the processes of Zeeman splitting and radiation absorption are identical or similar to the processes which take place in the sample cell 201. To this end, the magnetic field generator 103 provides a magnetic field 303 not only for the sample cell 201, but also for the reference cell 206. Thus, both the sample volume 304 and the reference volume 207 are penetrated by the modulated magnetic field 303.

An output signal of the reference UV light detector 107 is provided as a reference signal 308 for the evaluation unit 108.

The evaluation unit 108 may then evaluate the output signal 110, e.g., an oxygen concentration in the sample volume 304 of the sample cell 201 on the basis of both the measurement signal 307 output from the UV light detector 102 and the reference signal 308 output from the reference UV light detector 107.

Furthermore, the evaluation unit 108 is configured for receiving this measured reference signal 308 indicative of the oxygen concentration in the reference cell 206 such that the oxygen concentration in the sample volume 304 may be determined on the basis of the reference signal 308.

According to an exemplary embodiment of the present disclosure, a calibration curve may be provided which can be stored in a memory (e.g., a non-transitory computer-readable recording medium such as a hard disk drive, optical memory, flash memory, etc.) of the evaluation unit 108. According to an exemplary embodiment, the evaluation unit 108 can include a processor which executes a computer program recorded on such a non-transitory computer readable recording medium for carrying out the functions of the evaluation unit 108 as described herein. Such kind of calibration curve may be obtained from measurements with a known oxygen concentration in the sample volume 304. A curve of the measurement signal 307 may then be acquired as a function of a varying oxygen concentration in the sample volume 304 and may be stored as the calibration curve.

It is noted here that, in order to carry out the oxygen concentration measurements, the UV light source 101 emits a radiation in the wavelength region between 80 nm and 380 nm, e.g., in the region between 150 nm and 250 nm, e.g., a wavelength of about 130 nm or 184.9 nm. The term "about 130 nm" or "about 184.9 nm" means that the wavelength of the UV light source 101 is near an absorption line of oxygen to be measured. As used herein, the phrase "near an absorption line of oxygen" means that the absorption line of oxygen and the emitting line of the UV light source 101 are close enough such that the line profiles which are defined by the half-widths of the respective lines overlap each other, for example, in a manner differing as a function of applied magnet field, e.g., as a function of Zeeman wavelength splitting.

The UV light source 101 may be provided as at least one of a mercury lamp, a UV laser, a narrow band diode laser and a deuterium lamp. According to an exemplary embodiment, the deuterium lamp may contain mercury (Hg) such that emission lines of Hg are excited, and the UV light source 101 emits spectral lines of the mercury spectrum. This can result in a more efficient absorption of the UV radiation emitted by the UV light source 101, because some of the Hg emission lines coincide, at least partially, with absorption lines of oxygen, e.g., with the OI 184.95 nm absorption line.

The control unit 105 is configured for controlling the UV light source 101. Such a control may include the switching of the UV light source 101, a modulation in radiation intensity, etc.

In accordance with an exemplary embodiment, the reference UV light detector 107 may directly measure a portion of the first UV radiation intensity 301 to provide, for example, a reference signal for the radiation intensity of the UV light source 101. In this case, the reference cell 206 is not present in the reference detector optical axis 306. An advantage of such a configuration is that even if the radiation intensity of the UV light source 101 varies, and in consequence the radiation intensity measured at the UV light detector 102 varies even for a constant oxygen concentration in the sample volume 304, this radiation intensity variation of the UV light source 101 may be taken into account and its influence on the output signal 110 may be eliminated.

FIG. 5 is a detailed block diagram of an oxygen concentration measuring device 100 according to an exemplary embodiment of the present disclosure. The oxygen concentration measuring device 100 according to FIG. 5 includes two polarizing elements 204, in addition to the oxygen concentration measuring device 100 shown in FIGS. 3 and 4. One polarizing element 204 is arranged at the optical exit of the UV light source 101, and the other polarizing element 204 is arranged in front of the UV light detector 102.

Using both polarizing elements 204, it is possible to irradiate the sample volume 304 by means of a polarized first UV radiation intensity 301 and to detect a polarized second UV radiation intensity 302 in accordance with the setting of both polarizing elements. When the first UV radiation intensity 301 has a circular polarization, then the up-shifted and down-shifted Zeeman components in the second UV radiation intensity 302 have different polarization directions, e.g., a left-handed polarization for one component and a right-handed polarization for the other component.

Thus, it is possible, by using the second polarizing element 204 arranged in front of the UV light detector 102, for one of the two components to be filtered out. In combination with a varying magnetic field 303, it is thus possible to scan an oxygen absorption line over the central wavelength which is provided in the first UV radiation intensity 301. Except for the polarizing elements 204, the arrangement of the oxygen concentration measuring device 100 is similar to the concentration measuring device 100 shown in FIG. 4.

According to an exemplary embodiment of the present disclosure, the magnetic field generator is a first magnetic field generator. Furthermore, a second magnetic field generator is provided which is adapted for applying a magnetic field at the sample volume 304. The first and second magnetic field generators are adapted for applying mutually perpendicular magnetic fields. This results in a polarized second UV radiation intensity 302 in directions such that a signal-to-noise ratio may be increased by gating the output using a fixed polarizing element 204 arranged in front of the UV light detector 102.

Figure 6:
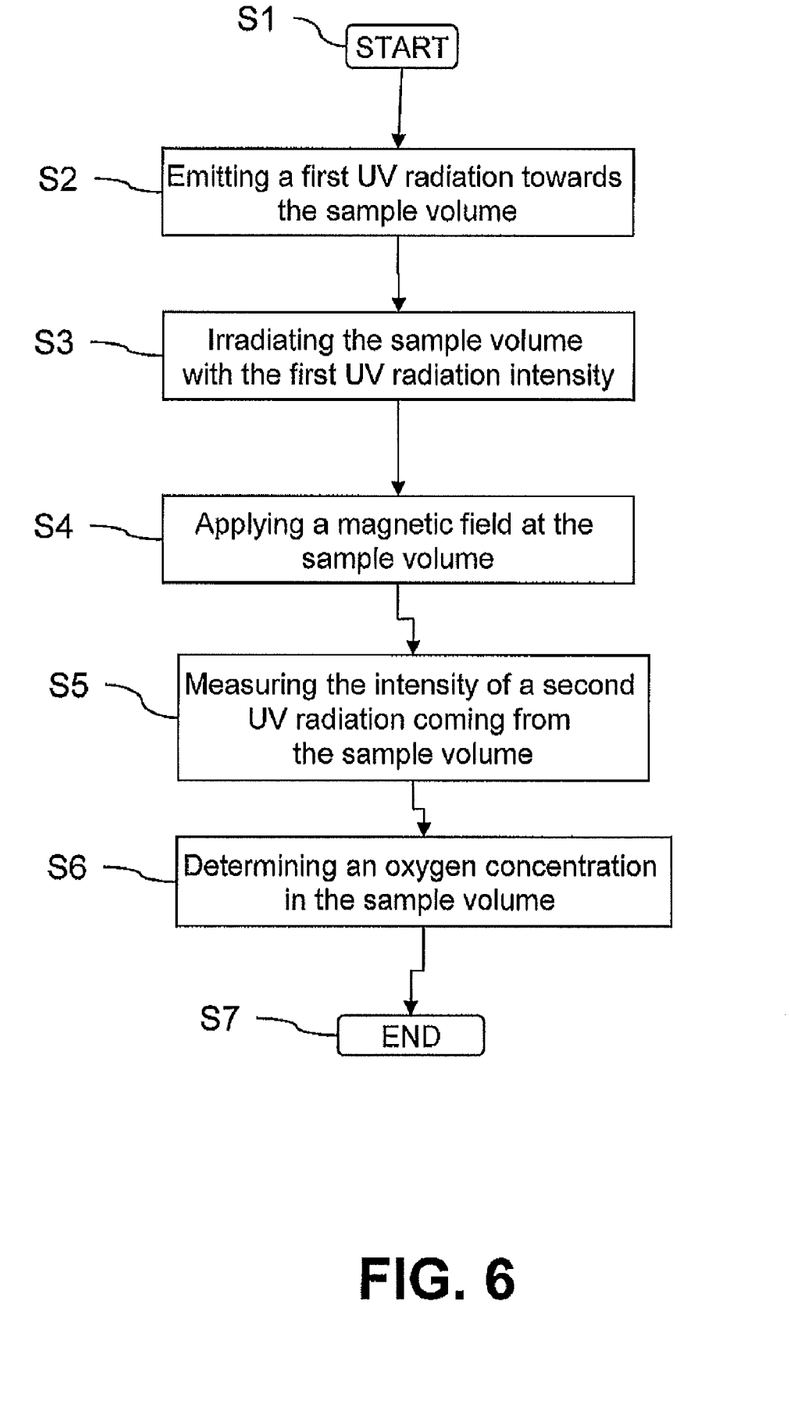
FIG. 6 shows a flowchart illustrating a method for determining an oxygen concentration in a sample volume according to an exemplary embodiment of the present disclosure.

FIG. 6 is a flowchart illustrating a method for determining an oxygen concentration in a sample volume according to an exemplary embodiment of the present disclosure. At step S1, the procedure starts. At step S2, a first UV radiation intensity is emitted towards the sample volume. The UV radiation includes at least one wavelength which is close to a spectral absorption line of oxygen. Then, the procedure advances to step S3 where the sample volume which contains an oxygen concentration to be measured is irradiated with the first UV radiation intensity.

Furthermore at step S4, a magnetic field is applied at the sample volume. The procedure advances to step S5 and an intensity of a second radiation coming from the sample volume is measured. The second UV radiation intensity is different from the first UV radiation intensity because a part of the first UV radiation intensity is absorbed by oxygen contained in the sample cell. From the difference intensity between the first UV radiation intensity and the second UV radiation intensity, an oxygen concentration in the sample volume is determined at step S6. Then, the procedure advances to step S7 where it is ended.

The magnetic field which is applied at step S4 may be modulated sinusoidally between a minimum magnetic field value and a maximum magnetic field value in order to obtain an appropriate Zeeman splitting of the spectral absorption line of oxygen which is close to the wavelength of the UV radiation incident in the sample volume. Furthermore, it is possible to change or reverse a polarity of the magnetic field which is applied at the sample volume. Moreover, the magnetic field may be changed periodically between an essentially constant on-value in an on-state and a zero magnetic field value in an off-state.

According to an exemplary embodiment, a magnetic field may be applied at the UV light source 101 in addition to or instead of applying the magnetic field at the sample volume 304. If the magnetic field is applied at the UV light source 101, then emission lines of the UV light source are Zeeman-shifted resulting in a similar oxygen concentration detection mode as the one described above. In addition, the application of a magnetic field at the UV light source 101 may provide a fine-tuning of at least one emission wavelength of the UV light source 101.

On the basis of the provided Zeeman-shift, more than one spectral absorption line of oxygen may be probed such that a vibrational molecule temperature of oxygen (oxygen molecule) and/or a rotational molecule temperature of oxygen (oxygen molecule) may be determined by probing respective vibrational molecule bands and/or rotational molecule bands, respectively. Such kind of probing may include a scan across at least a part of a rotational or vibrational spectrum (ro-vibrational spectrum) such that at least two absorption lines of an oxygen molecule are involved in the absorption process described herein above. If two or more absorption lines are probed or "scanned" (e.g., a rotational and/or a vibrational band of oxygen), then temperature information may be obtained in addition to species density (oxygen concentration) information. In an oxygen molecule, the absorption lines of a rotational band are closer to each other as compared to the absorption lines in a vibrational band. Thus, a Zeeman shift for probing vibrational molecule bands has to be larger than a Zeeman shift for probing rotational molecule bands.

Application fields of the oxygen concentration measuring device 100 according to any one of the described embodiments include industrial control devices where a concentration of oxygen shall be measured and/or monitored. Furthermore, in environmental monitoring and medical monitoring the oxygen concentration is a critical issue in many cases. In addition, combustion processes for which a specific oxygen concentration has to be provided can be monitored using the oxygen concentration measuring device 100 according to any one of the embodiments described above.

The disclosure has been described on the basis of embodiments which are shown in the appended drawings and from which further advantages and modifications emerge. However, the disclosure is not restricted to the embodiments described in concrete terms, but rather can be modified and varied in a suitable manner. It lies within the scope to combine individual features and combinations of features of one embodiment with features and combinations of features of another embodiment in a suitable manner in order to arrive at further embodiments.

It will be apparent to those skilled in the art, based upon the teachings herein, that changes and modifications may be made without departing from the disclosure and its broader aspects. That is, all examples set forth herein above are intended to be exemplary and non-limiting.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

REFERENCE NUMERALS 100 oxygen concentration measuring device
101 UV light source
102 UV light detector
103 magnetic field generator
104 optical focusing unit
105 control unit
106 frequency generator unit
107 reference UV light detector
108 evaluation unit
109 output unit
110 output signal
201 sample cell
202 phase comparator unit
203 UV transmissive window
204 polarizing element
205 beam splitter unit
206 reference cell
207 reference volume
300 optical axis
301 first UV radiation intensity
302 second UV radiation intensity
303 magnetic field
304 sample volume
305 polarization analyzer
306 reference detector optical axis
307 measurement signal
308 reference signal
309 oxygen concentration signal
310 reference radiation intensity
311 incident first UV radiation intensity
312 modulation signal
313 lock-in signal
314 frequency signal

What is claimed is:

1. An oxygen concentration measuring device configured for determining an oxygen concentration of a gas in a sample volume containing oxygen, the oxygen concentration measuring device comprising:
   an optical device configured for irradiating the sample volume with a first UV radiation having a first UV radiation intensity, the optical device including a UV light source configured for emitting the first UV radiation, the first UV radiation including at least one wavelength which is close to a spectral absorption line of oxygen;
   a magnetic field generator configured for applying a magnetic field at the sample volume;
   a UV light detector configured for measuring a second UV radiation intensity of a second UV radiation coming from the sample volume;
   an evaluation unit configured for determining the oxygen concentration in the sample volume on the basis of the applied magnetic field and the measured second UV radiation intensity; and
   a reference cell which contains oxygen of a reference concentration,
   wherein the evaluation unit is configured for receiving a measured oxygen concentration reference signal indicative of the oxygen concentration in the reference cell, and for determining the oxygen concentration in the sample volume on the basis of the oxygen concentration reference signal.

2. The oxygen concentration measuring device in accordance with claim 1, comprising:
   a sample cell having a UV transmissive window and containing the sample volume,
   wherein the optical device is arranged essentially outside the sample cell to irradiate the sample volume through the UV transmissive window of the sample cell.

3. The oxygen concentration measuring device in accordance with claim 2, wherein the optical device includes a polarizing element configured for providing polarized first UV radiation in the sample volume.

4. The oxygen concentration measuring device in accordance with claim 1, wherein the magnetic field generator is configured for further applying a magnetic field at the reference cell.

5. The oxygen concentration measuring device in accordance with claim 4, comprising:
   a reference UV light detector configured for measuring an intensity of at least a portion of the first UV radiation as a UV light reference signal,
   wherein the evaluation unit is configured for receiving the UV light reference signal from the reference UV light detector and for using the UV light reference signal for determining the oxygen concentration.

6. The oxygen concentration measuring device in accordance with claim 5, wherein the optical device includes a polarizing element configured for providing polarized first UV radiation in the sample volume.

7. The oxygen concentration measuring device in accordance with claim 5, wherein the magnetic field generator is a first magnetic field generator,
   wherein the oxygen concentration measuring device comprises a second magnetic field generator configured for applying a magnetic field at the sample volume, and
   wherein the first and second magnetic field generators are configured for applying mutually perpendicular magnetic fields.

8. The oxygen concentration measuring device in accordance with claim 1, wherein the UV radiation emitted by the UV light source has a wavelength in the region between 80 nm and 380 nm.

9. The oxygen concentration measuring device in accordance with claim 8, wherein the UV radiation emitted by the UV light source has a wavelength in the region between 150 nm and 250 nm.

10. The oxygen concentration measuring device in accordance with claim 8, wherein the UV radiation emitted by the UV light source has a wavelength of about 185 nm.

11. The oxygen concentration measuring device in accordance with claim 1, wherein the UV light source is one of a mercury lamp, a UV laser, a narrow band diode laser, a deuterium lamp, and a combination thereof.

12. The oxygen concentration measuring device in accordance with claim 11, wherein the UV light source is a combination of a lamp with a discrete spectrum and a lamp with a continuous spectrum in the frequency region in which the second UV radiation intensity is measured.

13. The oxygen concentration measuring device in accordance with claim 12, wherein the UV light source is a combined deuterium-mercury lamp.

14. The oxygen concentration measuring device in accordance with claim 1, comprising:
   a reference UV light detector configured for measuring an intensity of at least a portion of the first UV radiation as a UV light reference signal,
   wherein the evaluation unit is configured for receiving the UV light reference signal from the reference UV light detector and for using the UV light reference signal for determining the oxygen concentration.

15. The oxygen concentration measuring device in accordance with claim 1, wherein the optical device includes a polarizing element configured for providing polarized first UV radiation in the sample volume.

16. The oxygen concentration measuring device in accordance with claim 1, wherein the magnetic field generator is a first magnetic field generator,
wherein the oxygen concentration measuring device comprises a second magnetic field generator configured for applying a magnetic field at the sample volume, and
wherein the first and second magnetic field generators are configured for applying mutually perpendicular magnetic fields.

17. A method for determining an oxygen concentration in a sample volume containing oxygen, the method comprising:
emitting a first UV radiation from a UV light source towards the sample volume, the UV radiation including at least one wavelength which is close to a spectral absorption line of oxygen;
irradiating the sample volume with the first UV radiation;
applying a magnetic field at the sample volume;
measuring the intensity of a second UV radiation coming from the sample volume;
determining the oxygen concentration in the sample volume on the basis of the applied magnetic field and the measured intensity of the second UV radiation;
performing a calibration of the evaluated signal versus an actual oxygen concentration at least one of continuously and intermittently during operation by reference measurements with a reference oxygen cell.

18. The method in accordance with claim 17, comprising:
modulating the magnetic field essentially sinusoidally between a minimum magnetic field value and a maximum magnetic field value.

19. The method in accordance with claim 18, comprising:
reversing a polarity of the magnetic field periodically.

20. The method in accordance with claim 18, comprising:
changing the magnetic field periodically between an essentially constant on-value in an on-state and zero magnetic field value in an off-state.

21. The method in accordance with claim 18, comprising:
applying a magnetic field at the UV light source such that emission lines of the UV light source are shifted with respect to at least one oxygen absorption line.

22. The method in accordance with claim 17, comprising:
reversing a polarity of the magnetic field periodically.

23. The method in accordance with claim 22, comprising:
applying a magnetic field at the UV light source such that emission lines of the UV light source are shifted with respect to at least one oxygen absorption line.

24. The method in accordance with claim 17, comprising:
changing the magnetic field periodically between an essentially constant on-value in an on-state and zero magnetic field value in an off-state.

25. The method in accordance with claim 24, comprising:
applying a magnetic field at the UV light source such that emission lines of the UV light source are shifted with respect to at least one oxygen absorption line.

26. The method in accordance with claim 17, comprising:
applying a magnetic field at the UV light source such that emission lines of the UV light source are shifted with respect to at least one oxygen absorption line.

27. The method in accordance with claim 26, comprising:
determining a vibrational molecule temperature of oxygen by probing vibrational molecular bands.

28. The method in accordance with any claim 26, comprising:
determining a rotational molecule temperature of oxygen by probing rotational molecular bands.

29. The method in accordance with claim 26, comprising:
determining a vibrational molecule temperature of oxygen by probing vibrational molecular bands.

30. The method in accordance with any claim 26, comprising:
determining a rotational molecule temperature of oxygen by probing rotational molecular bands.

31. The method in accordance with claim 26, comprising:
adjusting the wavelength of the UV light source to coincide with a wavelength of an oxygen absorption line such that Zeeman-effect induced shifts of the oxygen absorption line for left and right circularly polarized radiation cause a difference in absorption for left and right circularly polarized radiation.

32. The method in accordance with claim 31, comprising:
measuring intensities of the left circularly second UV radiation and of the right circularly second UV radiation; and
determining the oxygen concentration in the sample volume on the basis of the measured intensities.

33. The method in accordance with claim 32, comprising:
determining the oxygen concentration in the sample volume on the basis of at least one of a ratio of the measured left and right circularly polarized second radiation, and a difference of the measured left and right circularly polarized second radiation divided by their sum.

34. The method in accordance with claim 26, comprising:
applying a magnetic field for the reference cell.

35. The method in accordance with claim 17, comprising:
adjusting the wavelength of the UV light source to coincide with a wavelength of an oxygen absorption line such that Zeeman-effect induced shifts of the oxygen absorption line for left and right circularly polarized radiation cause a difference in absorption for left and right circularly polarized radiation.

36. The method in accordance with claim 35, comprising:
measuring intensities of the left circularly second UV radiation and of the right circularly second UV radiation; and
determining the oxygen concentration in the sample volume on the basis of the measured intensities.

37. The method in accordance with claim 36, comprising:
determining the oxygen concentration in the sample volume on the basis of at least one of a ratio of the measured left and right circularly polarized second radiation, and a difference of the measured left and right circularly polarized second radiation.

38. The method in accordance with claim 17, comprising:
applying a magnetic field for the reference cell.

* * * * *